United States Patent
Mailova et al.

(10) Patent No.: US 9,402,863 B2
(45) Date of Patent: Aug. 2, 2016

(54) METHODS AND SYSTEMS FOR CONDITIONING IN SURGERY

(71) Applicant: ENDOSTAT NV, Leuven (BE)

(72) Inventors: Karina Mailova, Moscow (RU); Leila Adamyan, Moscow (RU)

(73) Assignee: ENDOSAT NV, Leuven (BE)

(*) Notice: Subject to any disclaimer, the term of this patent is extended or adjusted under 35 U.S.C. 154(b) by 165 days.

(21) Appl. No.: 13/942,349

(22) Filed: Jul. 15, 2013

(65) Prior Publication Data

US 2013/0303976 A1 Nov. 14, 2013

Related U.S. Application Data

(63) Continuation-in-part of application No. 13/582,866, filed as application No. PCT/EP2011/053405 on Mar. 7, 2011, now abandoned.

(30) Foreign Application Priority Data

Mar. 5, 2010 (GB) .................................. 1003682.0

(51) Int. Cl.

| | |
|---|---|
| *A61K 33/00* | (2006.01) |
| *A61M 13/00* | (2006.01) |
| *A61K 31/727* | (2006.01) |
| *A61K 45/06* | (2006.01) |
| *A61K 31/355* | (2006.01) |
| *A61K 31/375* | (2006.01) |
| *A61K 31/573* | (2006.01) |

(52) U.S. Cl.
CPC ............... *A61K 33/00* (2013.01); *A61K 31/355* (2013.01); *A61K 31/375* (2013.01); *A61K 31/573* (2013.01); *A61K 31/727* (2013.01); *A61K 45/06* (2013.01); *A61M 13/003* (2013.01); *A61M 2202/0208* (2013.01); *A61M 2202/0283* (2013.01)

(58) Field of Classification Search
CPC .............. A61M 13/00; A61M 13/003; A61M 2202/0208; A61M 2202/0283; A61M 2202/0225; A61M 2202/0241
See application file for complete search history.

(56) References Cited

U.S. PATENT DOCUMENTS

| | | | |
|---|---|---|---|
| 6,248,500 B1 | 6/2001 | Mizutani et al. | |
| 8,172,788 B2 | 5/2012 | Koninchx et al. | |
| 2002/0020462 A1* | 2/2002 | Wagenheim | A61M 16/12 141/200 |
| 2002/0183687 A1* | 12/2002 | Koninckx | 604/24 |

(Continued)

FOREIGN PATENT DOCUMENTS

WO 2004096315 A2 11/2004

OTHER PUBLICATIONS

International Search Report for PCT/EP2011/053405, Jun. 27, 2011.

(Continued)

*Primary Examiner* — Quynh-Nhu H Vu
(74) *Attorney, Agent, or Firm* — Workman Nydegger

(57) ABSTRACT

A method for preventing mesothelial cell trauma is described. The method comprises applying at pool of conditioning techniques prior and/or during surgery for decreasing detrimental factors and optimally using beneficial factors. The pool of conditioning techniques thereby comprises at least applying an irrigation liquid to irrigate at least part of the area of surgery wherein the irrigation liquid is a pH buffering liquid.

6 Claims, 5 Drawing Sheets

(56) References Cited

U.S. PATENT DOCUMENTS

| | | | |
|---|---|---|---|
| 2005/0107766 A1 | 5/2005 | Ott et al. | |
| 2005/0137529 A1* | 6/2005 | Mantell | 604/129 |
| 2006/0210602 A1* | 9/2006 | Sehl | A61L 17/145 424/423 |
| 2006/0229728 A1* | 10/2006 | McKay | 623/17.16 |
| 2007/0244449 A1* | 10/2007 | Najafi | A61K 9/0024 604/265 |
| 2007/0280990 A1* | 12/2007 | Stopek | A61F 13/00008 424/423 |
| 2008/0091233 A1* | 4/2008 | Ellis-Behnke et al. | 606/213 |
| 2011/0166506 A1* | 7/2011 | Ott | A61M 13/003 604/26 |
| 2012/0029654 A1* | 2/2012 | Xu et al. | 623/23.72 |
| 2012/0123202 A1* | 5/2012 | Albrecht | A61B 17/3417 600/104 |
| 2012/0330224 A1 | 12/2012 | Mailova et al. | |
| 2013/0211320 A1* | 8/2013 | Alkhamesi | A61M 13/003 604/24 |
| 2014/0370080 A1* | 12/2014 | Stucchi | A61K 31/19 424/450 |

OTHER PUBLICATIONS

International Preliminary Report on Patentability and Written Opinion for PCT/EP2011/053405, Sep. 11, 2012.

Tsereteli, et al., "Prospective Randomized Clinical Trial Comparing Nitrous Oxide and Carbon Dioxide Pneumoperitoneum for Laparoscopic Surger," Journal of the American College of Surgeons, vol. 195, No. 2, pp. 173-179, Aug. 2002.

Mynbaev, et al., "Effects of Adding Small Amounts of Oxygen to a Carbon Dioxide-pneumoperitoneum of Increasing Pressure in Rabbit Ventilation Models," Fertility and Sterility, Elsevier Science Inc. New York, NY, USA, vol. 92, No. 2, pp. 778-784, Aug. 1, 2009.

Neuman, et al., "Laparoscopy Explosion Hazards with Nitrous Oxide," Anesthesiology, vol. 78, No. 5, pp. 875-879, May 1993.

* cited by examiner

METHODS AND SYSTEMS FOR CONDITIONING IN SURGERY

The present application is a continuation in part of U.S. patent application Ser. No. 13/582,866, the description thereof being incorporated herein by reference.

FIELD OF THE INVENTION

The present invention relates to prevention or reduction of the consequences of the surgical environment upon a body cavity. More particularly, the present invention relates to the methods and systems combining materials and techniques for reducing or preventing the direct effect of the gas and fluid environment during surgery in a body cavity lined with a mesothelium.

BACKGROUND OF THE INVENTION

Many body organs, except muscles and bones, are situated in a body cavity lined with a mesothelium such as the peritoneal cavity, the thoracal cavity, and the cavity surrounding the heart, the brain and spinal cord. These are virtual cavities, with a small amount of fluid constituting a specific fluid microenvironment and with a mesothelium layer playing an active role in regulating transport of fluid and substances between the fluid of this cavity and the blood while helping the organs to glide in this cavity. The importance of this gliding is obvious for moving organs as bowels, heart and lungs.

In order to perform surgery in such a body cavity, the cavity has to be opened in order to create a working space. The microenvironment thus is disturbed and the mesothelial cell layer is exposed to rinsing liquids and to a gas environment which can be air in open surgery of CO2 during laparoscopic surgery. In order to create an adequate working space during laparoscopic abdominal surgery the pressure has in addition to be increased above the atmospheric pressure by at least 5 to 10 mm of Hg and generally 15 mm of Hg. Higher pressures are avoided out of fear of gas embolism although this limit has not been substantiated clinically.

Surgery with opening of a body cavity is associated with postoperative pain and with adhesion formation.

Best documented is adhesion formation occurring in over 50% of women following abdominal surgery. These adhesions remain a major clinical problem since they cause chronic pain, infertility, and the need for re-interventions. It is estimated that 30% of all infertilities, 30% of chronic pain, and 100% of bowel obstructions in women are caused by adhesions. Following surgery some 30% of women have to undergo repeat surgery of which 6% is directly and 29% indirectly related to adhesions, which increase the difficulty and complication rate of these surgeries as described by Lower, A. M. et al. in "Adhesion-related readmissions following gynaecological laparoscopy or laparotomy in Scotland: an epidemiological study of 24 046 patients." Hum. Reprod. 2004; 19, 1877-1885.

Postoperative pain is less understood. The somatic pain of the skin and other incisions is caused immediately by nerve lesions and subsequently by the inflammatory reaction, which is necessarily associated with the healing process. Visceral pain, e.g. from the pelvic cavity, on the contrary is known to be different. The nociceptors are specific. At rest nerve activity is low and most of the nociceptors are sleeping until activated. This explains that bowel movements are not painful under normal condition. Visceral pain moreover is more stretch than trauma related and proportional to the sum of neural firing activity and thus poorly localized with referred pain and often associated with vasomotor symptoms. Infection recruits and activates these nociceptors explaining that during peritonitis even bowel movements become extremely painful.

Prevention of postoperative pain does not yet exist and treatment is limited to the use of pain killers. There are no data describing the mechanism or the prevention of recruitment and/or activation of these nociceptors by the acute surgical trauma and the acute inflammation.

Prevention of postoperative adhesions has been limited to the suggested good surgical practice with gentle tissue handling and to barriers keeping injured areas separated for at least 5 days. This treatment was based upon the observations that surgical trauma is followed by an inflammatory reaction, with exudation and fibrin deposition and a well-known cascade of events leading either to healing within a few days or to adhesion formation. If the fibrin is rapidly removed by fibrinolysis, the entire area of trauma, irrespective of the area is healed within a few days, since proliferation of mesothelial cells starts from multiple areas. If the healing process is delayed for whatever reason, the growing fibroblasts or tissue repair cells will use the fibrin as a scaffold leading to adhesion formation. The mechanical separation of injured areas, by resorbable solid membranes or semi-solid gels results in a 40% to 50% reduction of adhesion formation as evidenced by repeat laparoscopy. These studies obviously were done for specific interventions as ovarian surgery and myomectomies only, whereas there are no data for clinically important endpoints as reintervention rate, fertility rates or severity of chronic pain.

The importance of the entire peritoneal cavity and of the specific microenvironment of the peritoneal fluid in postoperative pain and in adhesion formation was described over the last decade, mainly by the group of Philippe Koninckx. Key observations were the observation that manipulation of bowels in the upper abdomen enhanced adhesion formation in the pelvis pointing to substances released into the peritoneal fluid, as described in "Effect of Upper Abdomen Tissue Manipulation on Adhesion formation between Injured Areas in a Laparoscopic Mouse Model" by Shonman et al. in J. Minim Invasive Gynecol. 2009, 16(3) pp 307-312. The second key observation was that surgery is followed by acute inflammation (the phase preceding the inflammatory reaction) of the entire peritoneal cavity and that the severity of this acute inflammatory reaction is proportional to the enhanced adhesion formation, as described by Corona et al in "Postoperative inflammation in the abdominal cavity increases adhesion formation in a laparoscopic mouse model" in Fertil Steril 2011, 95(4) pp 1224-1228. The third observation was that the surgical trauma is essential for adhesion formation but that trauma alone causes quantitatively little adhesions, whereas factors from peritoneal fluid enhance the adhesion formation at the trauma site. The latter, peritoneal cavity enhanced adhesion formation is quantitatively 10 to 20 times more important than the surgical lesion by Koninckx PR et al. e.g. in The role of peritoneal cavity in adhesion formation, Fertil Steril 2011, 96(1) pp 193-197.

Experiments mainly in the mouse model for laparoscopic and for open surgery have delineated a series of good and bad factors enhancing or decreasing adhesion formation probably through acute inflammation. A bad factor is the CO2 pneumoperitoneum through superficial mesothelial hypoxia (defined as less than 10 mm Hg partial pressure) eventually ROS, and this effect is duration and pressure dependent as described by Molinas CR, Mynbaev O, Pauwels A, Novak P, Koninckx PR. In "Peritoneal mesothelial hypoxia during pneumoperitoneum is a cofactor in adhesion formation in a laparoscopic mouse model.", Fertil Steril 2001; 76:560-567. Equally detrimental is mesothelial hyperoxia, defined as a partial O2 pressure higher than 60 mm of Hg through at least ROS as described by Elkelani, O. A., Binda, M. M., Molinas, C. R. & Koninckx, P. R., in "Effect of adding more than 3% O2 to carbon dioxide PP on adhesion formation in a laparoscopic mouse model.", Fertil. Steril. 82, 1616-1622 (2004). Also strongly detrimental is desiccation as described by Binda M M, Molinas C R, Hansen P., Koninckx P R. In "Effect of desiccation and temperature during laparoscopy on adhesion formation in mice", Fertil Steril 2006; 86:166-175, blood especially fibrin and an increased peritoneal temperature. Beneficial factors identified so far are normoxia (defined as a partial oxygen pressure between 10 and 70 mm of Hg, or 2 to 6% of oxygen in the gas used for the pneumoperitoneum, as described in U.S. Pat. No. 6,428,500, cooling the peritoneal cavity with a third means which together with humidifying is protective through cooling and by eliminating any desiccation, as described in U.S. Pat. No. 8,172,788. The single most effective factor is N2O in concentrations of more than 5%, as described in U.S. patent application 2012/0330224. In the presence of 5 to 10% of N2O no or a marginal additive effect of O2 could be demonstrated as shown in FIG. 2.

All factors described as beneficial or detrimental in laparoscopic surgery were equally beneficial and detrimental in open surgery. Besides their effect on adhesion formation, it is not surprising that they were equally effective in reducing or promoting tumor cell implantation, and in, preventing or enhancing CO2 resorbtion during endoscopic surgery as described by Binda M M, Corona R, Amant F, Koninckx P R. in "Conditioning of the abdominal cavity reduces tumour implantation in a laparoscopic mouse model." Surgery Today 2013; in press. These factors also will prevent the progressively increasing CO2 resorbtion over time during laparoscopic surgery thus permitting surgery of longer duration which can be particularly important in obese patients and for surgery in strong Trendelenburg (FIG. 3). This effect is even more important when oxygenation of underlying tissues is considered. The progressively rising CO2 resorbtion and its prevention over time can only be explained by the fact that the intact mesothelial layer actively prevents diffusion of CO2 gas. Following retraction, diffusion of CO2 gas becomes quantitatively much more important which means that the depth of hypoxia progressively increases from initially some 100 μ to at least 3-4 mm. Hypoxia in deeper layers, albeit only a few mm becomes excessively important when considering thin organs as a bowel wall, especially during and after surgery, or and a remaining ovarian wall after excision of an ovarian cyst. Clinically this indeed translates to bowel perforations and leakage or to a decrease in ovarian reserve, two of the frequent complications of surgery.

SUMMARY OF THE INVENTION

It is an object of embodiments of the present invention to provide good systems and methods for assisting in surgery in any body cavity lined with a mesothelial cell layer. It is an advantage of embodiments of the present invention that systems and methods are provided allowing to prevent mesothelial damage and acute inflammatory reaction with retraction and bulging of the mesothelial cells. It is an advantage of embodiments of the present invention that such methods are beneficial for one or more and advantageously all direct and indirect consequences such as postoperative pain, adhesion formation, the speed of postoperative healing and recovery, the attachment of malignant or other cells to the denuded areas in between the retracted cells and for the effects upon the exchange between the cavity and the blood stream i.e. fluid, substances or gases.

It is an advantage of at least some embodiments according to the present invention that because of the unique mechanism of mesothelial cell retraction and acute inflammation, all beneficial and detrimental factors identified add up. The consequence of this is that a treatment or prevention should address more than one, preferentially address all factors instead of focusing on 1 factor or on the most relevant.

It is an advantage of embodiment of the present invention that the combined use of different preventions and treatments has the effect of a single action, addressing a single mechanism. The result of this is that a series of treatments that individually were not sufficiently effective to be clinically used, become important when used in combination with others.

It is an advantage of embodiments of the present invention that clinical result of this combined treatment are equally effective for any mesothelial lined cavity as the abdomen, the thoracal cavity, the heart and the central nervous system and the spine. It is an advantage of embodiments of the present invention that as a clinical result, during surgery less pain (only felt in the absence of anesthesia) is felt, that a decreased CO2 resorbtion during laparoscopy with CO2 pneumoperitoneum is obtained, and that the depth of tissue hypoxia is less. It is an advantage of embodiments of the present invention that after surgery less pain is present and a faster recovery and faster and better healing occurs. This translates in a faster mobilization (with all potential advantages as prevention of thrombosis) and a shorter hospitalization and shorter absence from work. This results in much less adhesion formation with less infertility, less chronic pain and less reoperation rate. This also results in a prevention of a decreased ovarian reserve after ovarian surgery, even a premature menopause, and a decreased incidence of late bowel perforations or leakage after bowel surgery. This also translates in a dramatic decrease in health expenditure for society.

The above object is obtained by a method and/or system according to the present invention.

The present invention relates to a method for preventing mesothelial cell trauma. The method comprises the application of a pool of conditioning techniques prior and/or during surgery, wherein the pool of conditioning techniques comprises an irrigation liquid to irrigate at least part of the area of surgery wherein the irrigation liquid is a pH buffering liquid, which is not cell toxic.

The pool of conditioning techniques furthermore may comprise applying a pneumoperitoneum comprising between 1 and 29 volume percentage of N2O.

The pool of conditioning techniques furthermore may comprise applying a pneumoperitoneum comprising between 1 and 6 volume percentage of oxygen.

The pool of conditioning techniques furthermore may comprise administering before and/or during surgery antioxidants, such as vitamin C or vitamin E.

The pool of conditioning techniques furthermore may comprise rinsing using a rinsing fluid comprising Heparin.

The heparin may be a high molecular weight heparin, the high molecular weight heparin having for example a molecular weight of more than 150000 daltons.

The pool of conditioning techniques may comprise separating areas not involved in the surgery from the area involved in the surgery using separation means.

The pool of conditioning techniques may comprise administering one or more of Dexamethasone, calcium channel blockers and phospholipids or antiprogestins.

The pool of conditioning techniques may comprise applying barriers for preventing noxious substances to reach the traumatized area and/or using flotation agents for diluting noxious substances.

The pool of conditioning techniques may comprise administering anti angiogenic agents, such as for example anti VEGF or anti PLFG monoclonals after surgery.

In an advantageous embodiment according to the present invention a combination of conditioning techniques is applied, the method comprising
  applying a pneumoperitoneum comprising between 1 and 29 volume percentage of N2O, administering before and/or during surgery anti-oxidants, such as vitamin C or vitamin E,
  rinsing using a rinsing fluid comprising Heparin,
  rinsing using a rinsing fluid which is not cell toxic(eg not saline) and with pH buffering capacity (to prevent the low pH induced by CO2)
  separating areas not involved in the surgery from the area involved in the surgery using separation means,
  administering one or more of Dexamethasone, calcium channel blockers and phospholipids, or anti-progestins
  applying barriers for preventing noxious substances to reach the traumatized area and/or wherein flotation agents are used for diluting noxious substances,
administering anti angiogenic agents, such as for example anti VEGF or anti PLFG monoclonals. The present invention furthermore relates to a method as described above whereby applying a pneumoperitoneum comprises applying a pneumoperitoneum further comprising between 1 and 6 volume percentage of oxygen for preventing hypoxia in deeper layers.

It is an advantage of embodiments of the present invention that it results in less CO2 resorbtion during surgery, much slower resorbtion of fluids after surgery, e.g. Ringers lactate becomes an effective flotation agent (FIG. 4), less pain after surgery, faster recovery and healing, less adhesion formation and its consequences. Furthermore, according to at least some embodiments of the present invention it results in absence of tissue ischemia during surgery, less damage to ovarian reserve after ovarian surgery and less risk of late bowel perforation after bowel surgery.

The present invention furthermore relates to an irrigation liquid for irrigating at least part of the area of surgery, the irrigation liquid comprising a pH buffering liquid. The irrigation liquid or rinsing liquid typically also may comprise glucose.

The present invention also relates to a set of products for use during surgery for preventing mesothelial cell trauma, the set of products comprising
  an irrigation liquid for irrigating at least part of the area of surgery, the irrigation liquid comprising a pH buffering liquid, and
one or more of
  a gas mixture for use as pneumoperitoneum or flowing over an open surgery area, the gas mixture comprising between 1 and 29 volume percentage of N2O,
  anti-oxidants, such as vitamin C or vitamin E,
  a rinsing fluid comprising Heparin,
  separation means for separating areas not involved in the surgery from the area involved in the surgery,
  one or more of Dexamethasone, calcium channel blockers and phospholipids, and antiprogestins or selective progesterone receptor modulators.
  barriers for preventing noxious substances to reach the traumatized area and/or flotation agents for diluting noxious substances,
  anti angiogenic agents, such as for example anti VEGF or anti PLFG monoclonals.

The gas mixture also may comprise between 1 and 6 volume percentage of oxygen.

The present invention also relates to a set of products for use during surgery for preventing mesothelial cell trauma, the set of products comprising
  an irrigation liquid for irrigating at least part of the area of surgery, the irrigation liquid comprising a pH buffering liquid
  a gas mixture for use as a pneumoperitoneum or for flowing over an open surgery area, the gas mixture comprising between 1 and 29 volume percentage of N2O and comprising between 3 and 6 volume percentage of oxygen,
  anti-oxidants, such as vitamin C or vitamin E,
  a rinsing fluid comprising Heparin,
  separation means for separating areas not involved in the surgery from the area involved in the surgery,
  one or more of Dexamethasone, calcium channel blockers and phospholipids, and antiprogestins or selective progesterone receptor modulators.
  barriers for preventing noxious substances to reach the traumatized area and/or flotation agents for diluting noxious substances,
  anti angiogenic agents, such as for example anti VEGF or anti PLFG monoclonals.

The present invention also relates to a conditioning system for use in surgery for preventing mesothelial cell trauma, the conditioning system comprising an irrigation unit for irrigating at least part of the area of surgery, the irrigation unit comprising an irrigation liquid comprising a pH buffering liquid which is not cell toxic (eg not saline).

The conditioning system furthermore may comprise one, more or all of a gas supply system comprising a gas supplying means adapted for providing a mixture of gas in or over a cavity wherein surgery is performed, the gas supply system being adapted for providing a mixture of gas for use as pneumoperitoneum in surgery comprising a carrier gas and between 1 volume percent and 29 volume percent nitrous oxide gas (N$_2$O), a moistening means for moistening a gas used, a heating and/or cooling means for controlling the temperature of the gas mixture, a cooling unit to cool the peritoneal cavity by a third means, a drug administering means for providing anti-oxidants, a drug administering means for providing one or more of dexamethasone, calcium channel blockers, phospholipids and antiprogestins or selective progesterone receptor modulators, a separation means for separating areas not involved in the surgery from the area involved in the surgery, a rinsing means for providing a rinsing fluid comprising Heparin, and a barrier gel providing means or a means for providing anti-angeiongic factors.

The present invention also relates to the use of a gas mixture comprising between 1 and 6 volume percentage of oxygen for preventing hypoxia in deeper layers. Preventing hypoxia may result in preventing bowel perforation and ovarfian damage and decreased ovarian reserve.

It also relates to a gas mixture comprising between 1 and 6 volume percentage of oxygen as a medicament preventing hypoxia in deeper layers. Preventing hypoxia in deeper layers may comprise preventing bowel perforation and ovarfian damage and decreased ovarian reserve.

Particular and preferred aspects of the invention are set out in the accompanying independent and dependent claims. Features from the dependent claims may be combined with features of the independent claims and with features of other dependent claims as appropriate and not merely as explicitly set out in the claims.

These and other aspects of the invention will be apparent from and elucidated with reference to the embodiment(s) described hereinafter.

Figure 1:
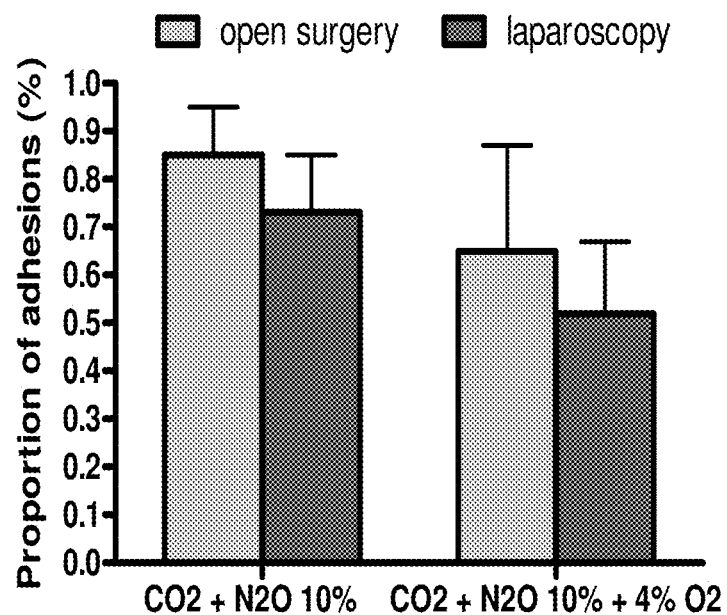
FIG. 1 describes in a mouse model a similar effect of conditioning upon adhesion formation in open and in laparoscopic surgery. It also demonstrates the marginal additional effect of adding 4% of O2 when 10% of N2O is used.
Figure 2:
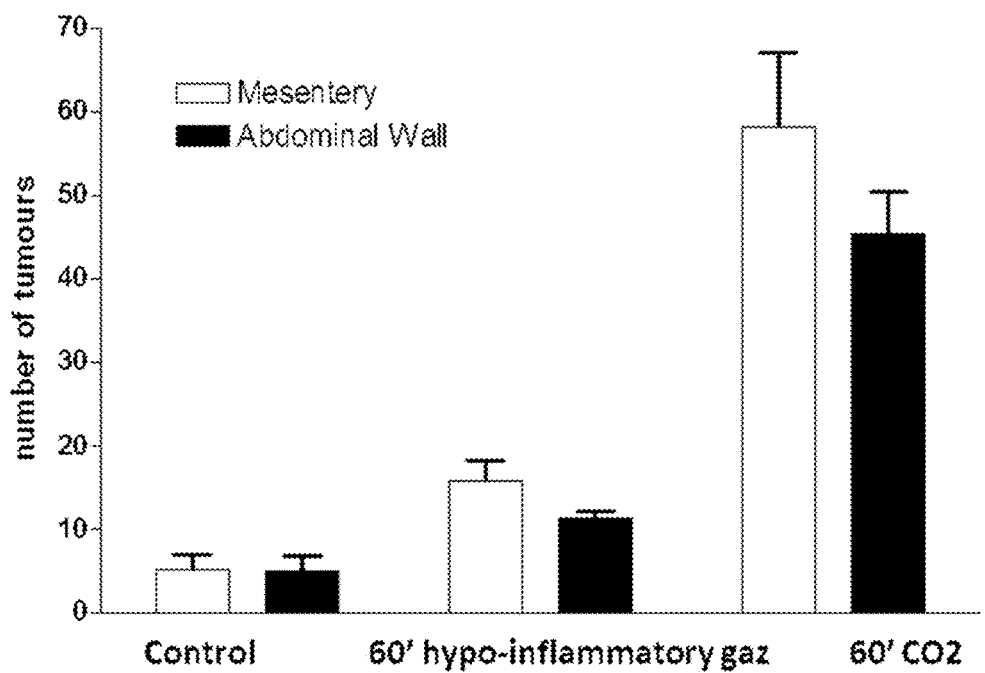
FIG. 2 demonstrate in a mouse model the increased implantation of cancer cells following a CO2 pneumoperitoneum for 60 min and its prevention by conditioning.
Figure 3:
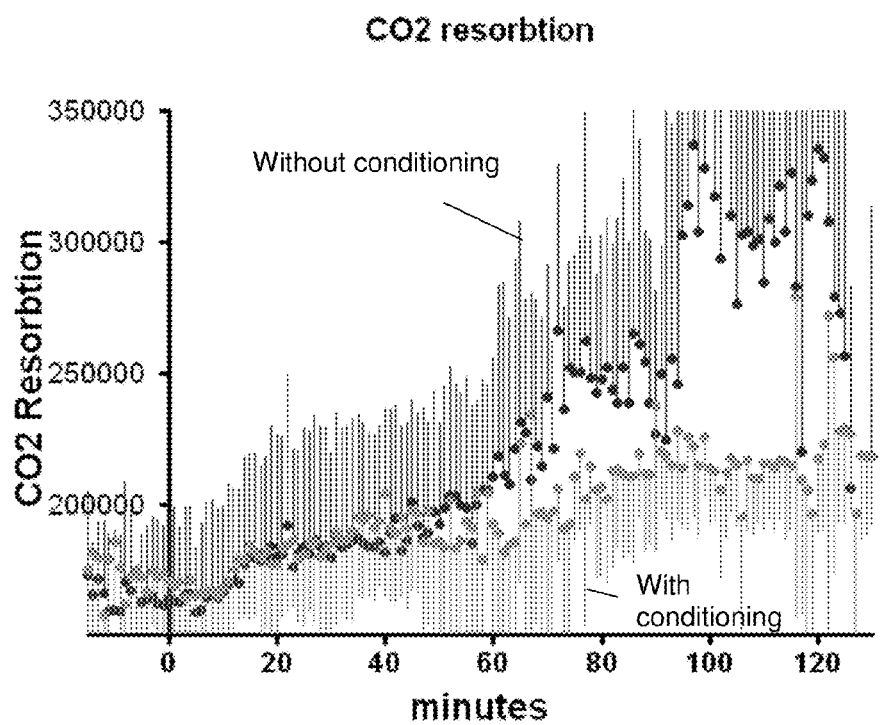
FIG. 3 demonstrate in the human the progressively increasing CO2 resorbtion of CO2 during CO2 pneumoperitoneum and its prevention by conditioning.

The drawings are only schematic and are non-limiting. In the drawings, the size of some of the elements may be exaggerated and not drawn on scale for illustrative purposes.

Any reference signs in the claims shall not be construed as limiting the scope.

DETAILED DESCRIPTION OF ILLUSTRATIVE EMBODIMENTS

Where in embodiments of the present invention reference is made to nitrous oxide gas, also known as happy gas or laughing gas, reference is made to the chemical compound having the chemical formula $N_2O$. At room temperature, it is a colorless gas.

Where in embodiments of the present invention reference is made to gas that is introduced in a cavity of the body of a living creature lined by a mesothelium reference is made to any cavity such as the abdominal cavity, the pericardium and the lung pleura of an animal or human being. More particularly, in embodiments of the present invention, reference is made to gas that is deliberately created, e.g. by the surgical team, for insufflating a cavity of the body of a living creature, e.g. the abdomen, and to gas that is deliberately introduced during laparotomy or laparoscopy or over the body of a living creature during open surgery for removing environmental air or unwanted gas present.

Where in embodiments of the present invention reference is made to laparotomy, reference is made to a surgical procedure involving an incision through the wall of the cavity, e.g. the abdominal wall, to gain access into the abdominal cavity. Where in embodiments of the present invention reference is made to laparoscopy, reference is made to an operation performed with the aid of an endoscope and a camera e.g. in the abdomen or pelvis through small incisions. Laparotomy also may be referred to as open surgery.

It should be noted that given the similarity of effects upon the mesothelial tissue between laparoscopic surgery and laparotomy, all beneficial aspects of embodiments of the present invention are equally applicable during laparoscopic surgery, laparotomy, also referred to as open surgery.

Where in embodiments of the present invention reference is made to a compound, the latter includes the combination of the products described with gels, e.g. for use in endoscopy.

After having realized that the driving mechanism was mesothelial cell trauma resulting in cell retraction and bulging, exposing directly the basal membrane, and acute inflammation and of deleterious factors secreted into the peritoneal fluid, a series of other factors and measures were either experimentally demonstrated or clinically evaluated. Indeed since the trauma/acute inflammation is the result of all beneficial and all detrimental factors combined, therapy and prevention should advantageously focus on all factors involved.

Full conditioning, thereby minimizing trauma to mesothelial cells and organs, can advantageously be used in a wide range of applications, four major applications being described below.

The first application of full conditioning obviously is prevention of pain and adhesion prevention following intra-abdominal surgery as demonstrated in a human RCT. Following deep endometriosis surgery, pain was much less, adhesions were virtually absent, clinical recovery and time to first flatus was shorter.

The second application is prevention of pain and adhesion formation during open surgery.

The third application is prevention of adhesions and/or preventing pain during thoracic, cardiac, spinal cord and brain surgery.

The last exemplary application is the prevention of late bowel perforation and of oocyte damage during abdominal surgery involving the ovary. A reduced oocyte reserve is a major problem especially following excision of cystic ovarian endometriosis, caused at least in part by hypoxia/acidosis of the remaining ovarian tissue, by the thickness of the ovarian flap and the duration of exposure to pure CO2. Full conditioning will prevent this. Similarly the risk of late bowel perforations as occurring after deep endometriosis surgery and following bowel resection should be reduced by preventing ischemia of the thin bowel wall.

In a first aspect, the present invention relates to a method for preventing mesothelial cell trauma, the method comprising applying a pool of conditioning techniques prior and/or during surgery, wherein the pool of conditioning techniques comprises at least applying an irrigation liquid to irrigate at least part of the area of surgery wherein the irrigation liquid is a pH buffering liquid.

The liquid used for irrigation during surgery should thus be mesothelial cell friendly. Hence the fluids used today are suboptimal. Physiologic—sodium chloride 0.9%—is only isotonic and is harmful to monolayer cell cultures which retract and bulge. Ringers lactate or Hartman are other frequently used solutions in prior art. Nevertheless, the inventors have realized however that they were designed for IV infusion especially in cases of metabolic acidosis, not for irrigation during surgery. For irrigation during surgery solutions as used during cell culture in vitro should be considered with in addition a buffer limiting the drop in pH because of the acidosis caused by CO2. This points to at least a phosphate buffered saline (PBS), eventually a richer medium as used during cell cultures supplemented with bicarbonate or a specific buffering substance.

Advantageously, the method comprises applying a pool of conditioning techniques, whereby the conditioning techniques used may comprise one or more of the techniques described below.

In one embodiment, the method comprises applying a compound as a pneumoperitoneum or a gas flowing over the cavity during open surgery for replacing environmental air or other unwanted gasses. The compound comprises a carrier gas, such as for example carbon dioxide gas ($CO_2$), and between 1% and 29% nitrous oxide gas ($N_2O$). The upper limit thereby is amongst others determined by the explosion risk at higher concentrations. In some embodiments, the compound consists of a carrier gas and nitrous oxide gas ($N_2O$), while no other components are intentionally added to the compound. The carrier gas and any added gas in concentrations over 4% advantageously have a solubility larger than 0.5 g/l in water. It has surprisingly been found that the use of nitrous oxide gas has advantageous effects on reduction or prevention of adhesion formation. The compound may in some embodiments for example comprise between 1 and 29 volume percentage nitrous oxide gas, preferably between 5 and 20 volume percentage nitrous oxide gas, more preferably between 5 and 10 volume percentage nitrous oxide gas. The remaining part may be or may mainly be the carrier gas, such as for example pure carbon dioxide gas. Obviously other gases, such as helium, could be used as carrier gas, although this would conflict with the safety requirements during laparoscopy. $CO_2$ is generally used for pneumoperitoneum since $CO_2$ is highly soluble in water and since $CO_2$ has a high exchange capacity in the lungs. N2O moreover has an ever higher solubility in water than CO2. The addition of a small amount of a poorly soluble gas, as e.g. O2 to the compound is considered clinically safe for gas embolism.

The compounds, which may be referred to as drugs, can be applied either systemically or by local instillation during surgery or by the prolonged administration intraperitoneally postoperatively, preferably locally, e.g. by miniosmotic pumps. Local administration has the advantage that much higher concentrations of active drugs or compounds can be provided by providing them over longer time. The administration can be performed for a plurality of hours postoperatively. More specifically the compounds can be coupled to a high molecular weight carrier, e.g. higher than 60.000 daltons and preferably more than 150.000 daltons ensuring a longer retention time.

In one embodiment, the compound also may comprise oxygen gas in the gas mixture, thus restoring a physiologic partial oxygen pressure in the cells in contact with the gaz. It has been demonstrated that oxygen, has little, clinically insignificant, effect on adhesion formation when more than 5% of nitrous oxide gas is used. Since N2O prevents the increased CO2 resorbtion and thus hypoxia in deeper tissue layers, the addition of small amounts of O2 remains important, no longer for adhesion prevention but for prevention of hypoxia in deeper layers and thus bowel perforation and ovarfian damage and decreased ovarian reserve. The compound thus may comprise carbon dioxide as major component, with additional nitrous oxide gas and oxygen gas. The concentration of oxygen gas used may be in the range 1% to 10%, e.g. 2% to 6%, e.g. 3%. In one embodiment, the pool of conditioning techniques comprises using an antioxidant, demonstrated to prevent adhesion formation in animal models. Considering the role of reactive oxygen species (ROS), it was demonstrated that the anti adhesiogenic effect of anti-oxidants used intraperitoneally in CO2 pneumoperitoneum enhanced adhesion formation. Therefore, one of the elements in the pool of conditioning techniques may comprise using an antioxidant. Typically all know antioxidants will exert a positive effect, for example Vitamin C and Vitamin E can advantageously be used, whether used intraperitoneally, eventually conjugated to a high molecular weight carrier molecule, or systematically.

Figure 5:
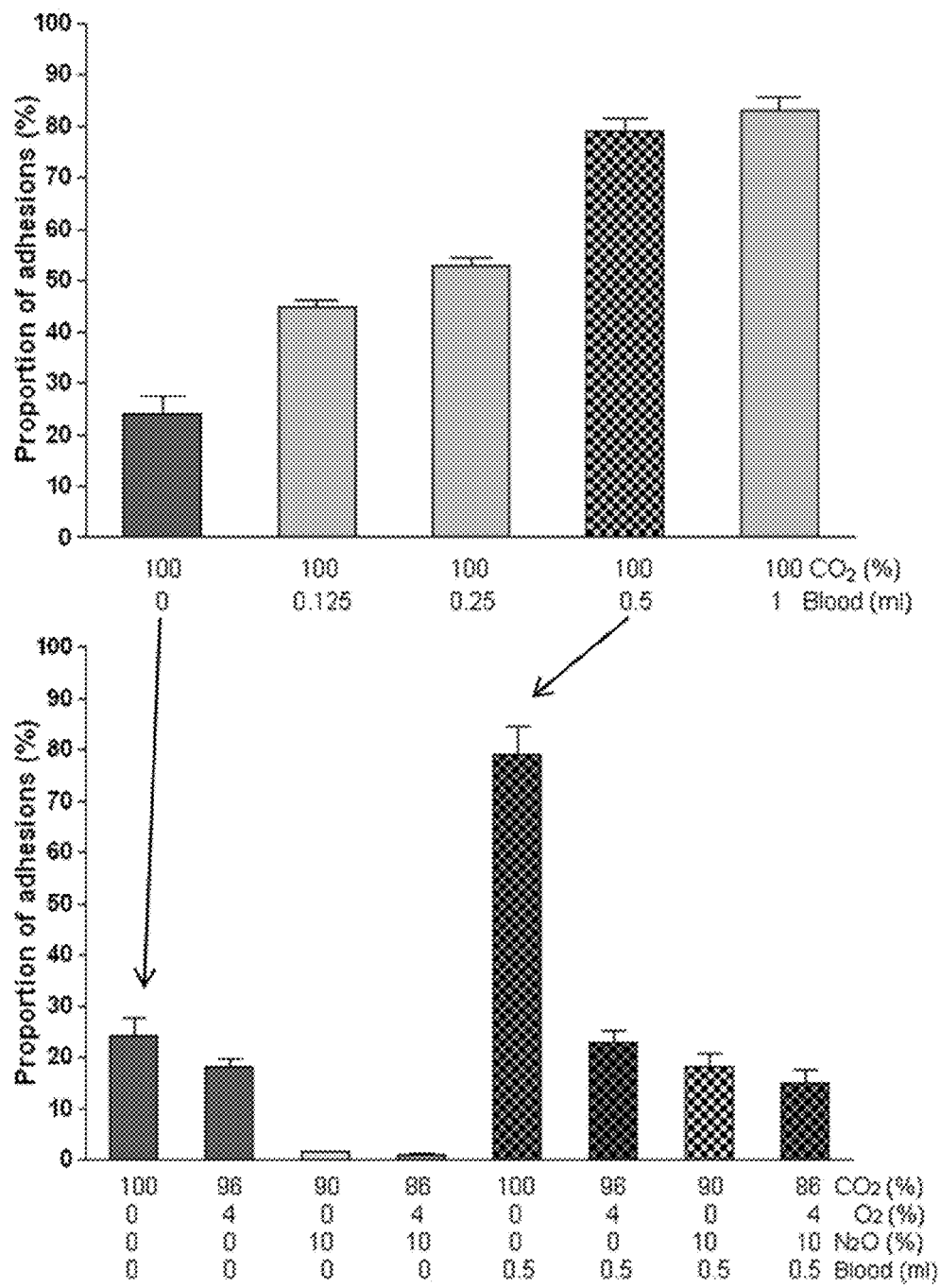
FIGS. 5 and 6 demonstrate the adhesiogenic effect of blood and of fibrin in particular, and the antiadhesiogenic effect of N2O in the presence of blood.
Figure 6:
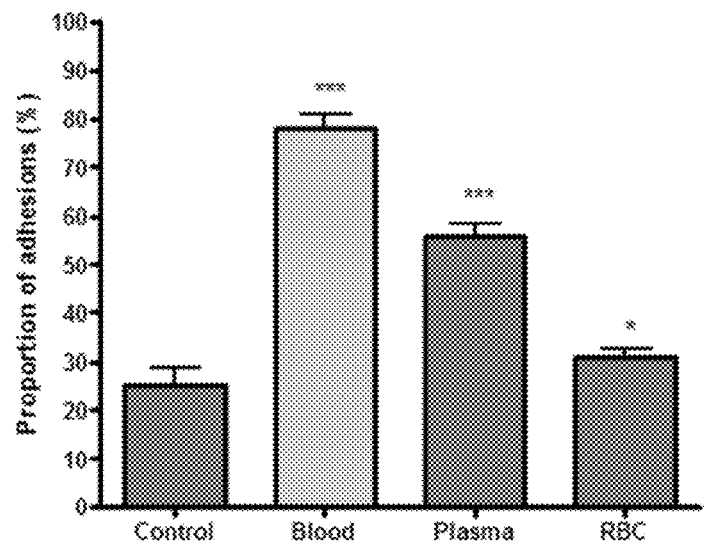

In one embodiment, the pool of conditioning comprises applying heparin to a rinsing fluid or a cooling fluid. Blood, especially fibrin, in the peritoneal cavity is strongly adhesiogenic as demonstrated in our mouse model (FIGS. 5 and 6), It thus is advantageous to limit the amount of fibrin left in the peritoneal cavity after surgery. This can obviously be done by adding heparin to the rinsing fluid or to the fluid used for cooling. The efficacy on adhesion prevention of adding heparin to the rinsing fluid, done to prevent clot formation in human surgery, has remained controversial in the past. This is not surprising given the variability in surgery, and since heparin was given to prevent clot formation in the area of surgery and not in order to prevent fibrin deposition in the entire peritoneal cavity, while little or no other factors of peritoneal cavity damage are controlled (since unknown). By demonstrating that fibrin removal is important, and by understanding that this can be achieved with heparin, and knowing that the permeability of the peritoneal cavity to molecules greater than 60 Dalton's is very slow, in one embodiment of the present invention the use of heparin in the rinsing fluid or even better in the fluid used for intermittent cooling is applied as advantageous conditioning technique. More importantly large molecule weight heparin—in contrast to the actual use of low molecular weight heparin for anticoagulation—should be preferred since less resorbed and thus less systemic effects with less risk of inducing postoperative bleeding.

Figure 7:
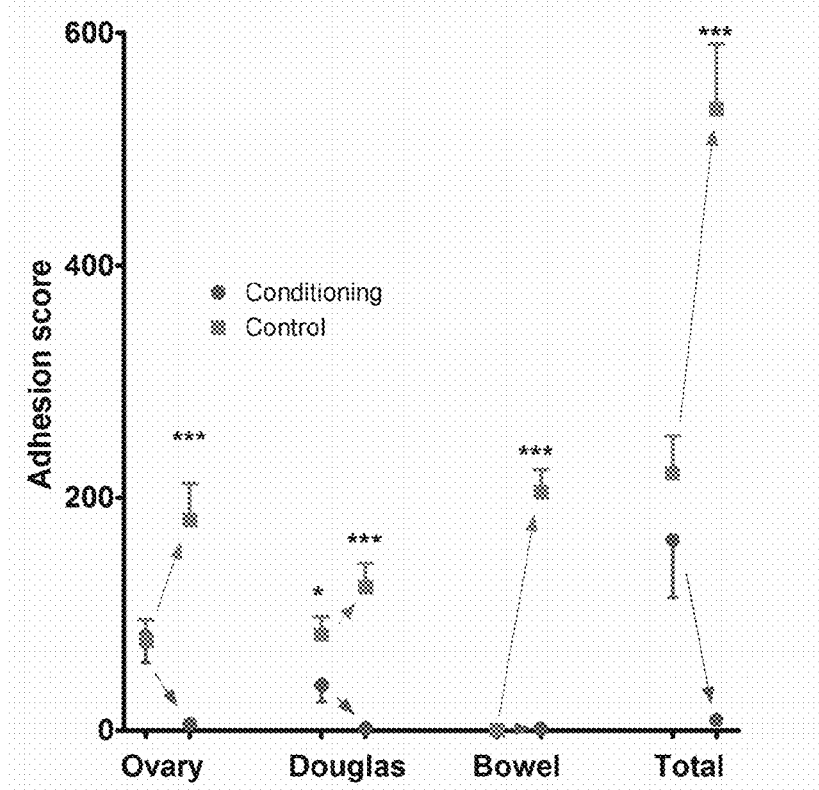
FIG. 7 describes the antiadhesiogenic effect of full conditioning (10% N2O, 4% of O2, heparin, cooling and humidification in the human.

During laparoscopic surgery with patients in Trendelenburg, fluid from the pelvis, rinsing fluid contaminated eventually with blood or worse following a bowel trauma, accumulates in the upper compartment around the liver. Clinically it is important to rinse at the end of surgery the upper compartment, which can be painstaking long often requiring more than 4 liters. It therefore is useful to leave at the beginning of surgery a few 100 ml of fluid in the upper abdomen, thus preventing fibrin deposition, and facilitating rinsing at the end of surgery. In addition it is logic to use an artificial diaphragm separating the pelvis from the abdominal cavity at the level of the umbilicus or the pelvic brim. An embodiment together with a trocar is illustrated in FIG. 7 A plastic shield is surrounded with a small circular balloon which following insufflation is anteriorly fixed to the trocar i.e. the umbilicus, and posteriorly positioned above the brim occluding laterally both paracolic gutters. This device in addition has the advantage of providing excellent bowel mobilization facilitating visualization during pelvic surgery.

This shield moreover compartementalises the peritoneal cavity during pelvic surgery, exposing a smaller area to the noxious effects to be prevented by conditioning.

Figure 4:
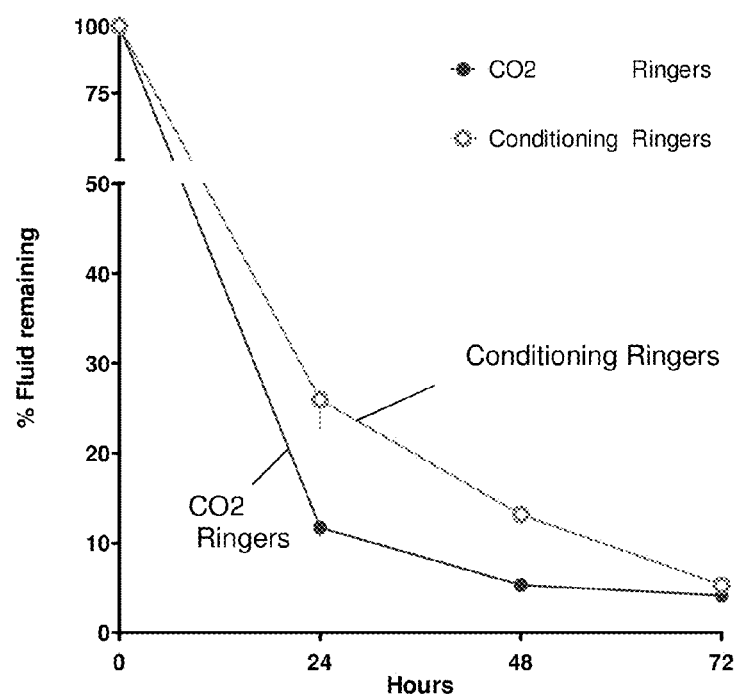
FIG. 4 demonstrate in the human that the rapid resorbtion of ringers lactate is decreased following conditioning.

Leaving a flotation fluid in the peritoneal cavity at the end of surgery remains controversial. Crystalline fluids as Ringers lactate have some efficacy in mice but little consistent efficacy in the human. Icodextrin 4% (Adept) was claimed to have a retention time of several days, which we demonstrated not to be true. Icodextrin 4% is marginally effective in adhesion prevention. We demonstrated recently (FIG. 4) that the retention time of ringers lactate is increased by peritoneal conditioning and becomes comparable to the retention time of 4% icodextrin (Adept), suggesting that in conjunction with conditioning the efficacy of Ringers lactate should be revisited.

In one embodiment, the pool of conditioning techniques comprises administering dexamethasone after surgery. Dexamethasone administered after surgery has been suggested for adhesion prevention, but the clinical efficacy was variable or absent. As learned from our mouse model however, when applying at least some and advantageously all of the conditioning factors, dexamethasone is highly effective in preventing adhesion formation. The exact mechanism is unknown, and can only be speculated upon. Interesting in this context is that anti-inflammatory agents as Cox1 and 2 inhibitors and anti-TNFa molecules did not affect adhesion formation.

In one embodiment, the pool of conditioning also comprises using fluids and/or drugs limiting or preventing ischemia reperfusion. It is well known in transplant surgery that reperfusion following ischemia is a major detrimental factor for which a series of fluids and measures have been devised. During laparoscopy the insufflation pressure causes some (superficial) ischemia with reperfusion at the end of surgery. All fluids and drugs designed to prevent ischemia reperfusion in transplant surgery thus could be equally effective in laparoscopic surgery. This becomes even more important when considering the hypoxia/ischemia caused by the increased adsorbtion of $CO_2$ during laparoscopic surgery without conditioning.

In one embodiment, the pool of conditioning techniques also comprises the moistening the gas mixture that is supplied or moistening the area of surgery, more particularly directly moistening the bodily parts in the cavity or open surgery area. The moistening may in one embodiment be performed by sprinkling. In one embodiment, the pool of conditioning techniques also may comprise heating and/or cooling the gas mixture or other products used. The latter may be performed in response to a temperature measurement, i.e. the gas supply system also may comprise a temperature measurement system for obtaining temperature information for the gas mixture. Most important is to cool the peritoneal cavity and to prevent any desiccation. In order to achieve this, the peritoeneal cavity has to be cooled with a third means, so that the humidifed gas will cause some condensation upon entrance. In one embodiment, the pool of conditioning also comprises administering one or more of drugs like calcium channel blockers, phospholipids and SPRM.

In one embodiment, additional drugs may be administered. Administering of drugs, continuously or intermittently e.g. via aerosol may comprise using activation of potassium channels, modulation of macrophage activation and leucocyte attraction through cytokines, or their inhibitors, the effect of VEGF expression being blocked by antibodies or other inhibitors, indomethacin which can inhibit the membrane lipid peroxidation products following anoxemia, prostaglandin El for reducing the consequences of ischemia and/or anoxemia in the liver, allopurinol for reducing the consequences of ischemia and/or anoxemia in the kuppfer cells of the liver through an effect on xanthine-oxidase, calcium channel blockers, free radical scavengers, lipid peroxysomes, pregnatrienes, calcium antagonists, prevention of hypoxia associated stress proteins, acidosis for preventing reperfusion damage, MP, dopamine and ATP-MgCl2 administered following the anoxemia. The dose of the above drugs or systems is determined taking into consideration the age, sex, and symptom of the disease of the subject, the desired therapeutic effect, the period of administration, etc.

In one embodiment, the pool of conditioning comprises the combination of different conditioning techniques. Before and during surgery antioxidatives (eg Vit C and E) are beneficial. During surgery the mesothelial area and the duration of exposure to damaging factors is kept minimal by a membrane. During surgery the gas environment is minimally damaging by using 5% of more of N2O instead of damaging gases as pure $CO_2$ or more than 10% Oxygen. During surgery, 2 to 4% of oxygen should be added in order to prevent ischemia and hypoxia of deeper tissue layers and ovarian and bowel damage, not for adhesion prevention. During surgery desiccation is prevented, and the mesothelial cell layer is cooled. During and at the end of surgery, fluids used for irrigation or flotation are not damaging and thus are more cell friendly with a normal pH in the presence of over 90% of $CO_2$, than fysiologic saline. During surgery fibrin deposition is prevented in the entire cavity. At the end of surgery dexamethasone is beneficial as demonstrated in mouse models. Also calcium channel blockers, phopholipids and SPRM are beneficial in adhesion prevention in mouse models, as are the prevention of consequences of the inflammatory reaction as fibroblast proliferation and angiogenesis (eg through anti VEGF or PlGF mon oclonals).

In conclusion, the understanding that the mechanism of adhesion formation (and postoperative pain) is driven by mesothelial damage with retraction, enhanced CO2 resorbtion and ischemia of deeper layers, and subsequently an acute inflammation may be a key element. Prevention of this mechanism can be multifactorial. Some known factors as 'gentle tissue handling' are understood differently from before. Some factors are new and unexpected as cooling of the peritoneal cavity and the effect of N2O. Some factors as adding small doses of O2 have to be revisited: when using N2O O2 indeed no longer is effective in preventing adhesion formation. It remains important however for preventing ischemia of deeper tissue layers and thus in the prevention of ovarian and bowel damage. Several factors were demonstrate to be effective (in animal models), but their isolated effectivity was either too limited, or too variable in poorly controlled animal models and generally both, to be demonstrated in clinical trials. Realizing the common driving mechanism of mesothelial damage in the entire peritoneal cavity, we were able to demonstrate for each of them specific and reliable adhesion prevention in mouse models in which all other damaging factors were strictly controlled. This we demonstrated for dexamethasone, heparin, calcium channel blockers, SPRM's, phospholipids, anti VEGF and PlGF monoclonals, antioxidants, factors blocking hypoxaemia inducible factor (HIF1 and HIF2) and for liquids used for irrigation based upon Hanks and Earle's balanced salt solutions in comparison with saline. The effect of factors as flotation agents was revisited by demonstrating the longer retention time of crystalloids in the human following conditioning. Most importantly is that most of these factors can readily be used since clinically be proven since many years to be safe. To demonstrate the importance of this concept we recently performed a randomized controlled trial in the human in women undergoing severe surgery for deep endometriosis. By combining N2O, O2, cooling and humidification, heparin and dexamethasone together with a barrier agent since a different mechanism of action we achieve a near 100% prevention of adhesion formation. (FIG. 7), much less postoperative pain and a faster recovery.

By way of illustration, embodiments of the present invention not being limited thereto, some examples and particular embodiments are discussed below, illustrating some features and advantages of some embodiments according to the present invention.

In one particular example a decrease of all detrimental factors to a minimum is combined with all beneficial factors. A device therefore can be used delivering CO2 with between 5% and 10% of N2O and between 2% to 4% of O2, either by premixing the 3 gases before the insufflator of by adding N2O and O2 after the insufflation. The device may be adapted for humidifying the gas and for heating it to 1 or 2% above the intraperitoneal temperature cooled to 28 to 30° C., thus causing some condensation upon entrance.

Figure 8:
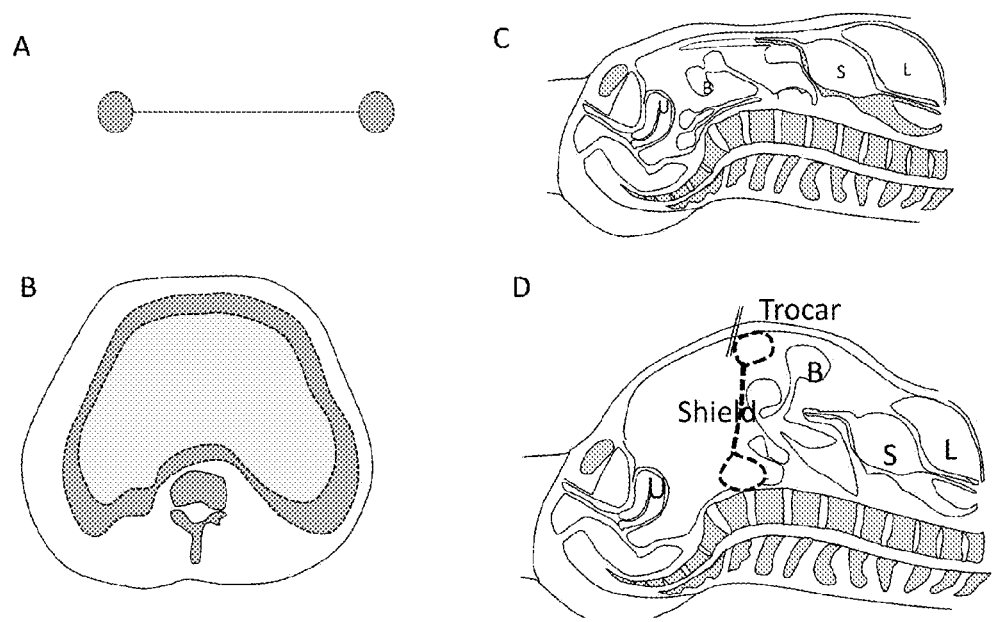
FIG. 8 (A to D) illustrates a shield to separate upper and lower abdomen as can be used in an embodiment according to the present invention, wherein FIG. A and B illustrate a shield being a membrane surrounded by an inflatable balloon with an heart shaped form, of 20-30 cm in diameter, surrounded by a balloon of 2 to 5 cm in diameter, Fig B illustrates the position of the shield in a transverse section of the abdomen, Fig C illustrates the virtual peritoneal cavity without insufflation and Fig D illustrates the peritoneal cavity after insufflation whereby the trocar and the shield are fixed anteriorly to the trocar and posteriorly above the brim with occlusion of the pararectal gutter. The shield is maintained in place by insufflating the circular balloon around the shield.

The above gas conditioning is combined with giving, before and/or during surgery, antioxidants as vitamin C or vitamin E either orally, IV, IM or intraperitoneally. Rinsing is performed with a cell culture like medium, i.e. with a medium at least supporting cell growth and survival for several hours, buffered to prevent the acidosis of CO2 pneumoperitoneum. Large molecular weight heparin is added to the rinsing or cooling fluid in order to prevent fibrin deposition. During e.g. pelvic surgery the upper abdomen is mechanically shielded from the pelvis (FIG. 8), thus minimalizing damage of bowels and upper peritoneal cavity, and minimalizing contamination of the upper abdomen by constituents from the pelvis. Following surgery dexamethasone is given either IM or intraperitoneally. In the absence of infection flotation with a non toxic fluid as used for irrigation is considered. In addition medical treatment during and after surgery is given in order to maintain integrity of the peritoneal cavity and peritoneal fluid. Medication used may be calcium channel blockers, phospholipids, SPRM, prevention of reperfusion trauma, and agents preventing vessel proliferation as anti VEGF or anti PLFG.

In another example, mortality in mice is discussed. A 100% mortality in mice considered to be caused by desiccation (after exposure of an open abdomen to air or CO2) was prevented not only by prevention of desiccation using humidified gas but also by the addition of small amounts of N2O or O2 to the CO2, something that obviously does not change desiccation. Small amounts of N2O prevented the specific adhesiogenic effect of blood in the abdomen. In the human it was surprisingly found that full conditioning of the abdominal cavity accelerated recovery clinically and the moment of first flatus. It was also surprisingly found that cooling could prevent the consequences of desiccation without affecting desiccation itself. It was furthermore surprisingly found that dexamethasone was highly effective in preventing adhesion formation if most of other mesothelial traumas had been addressed by conditioning. It is an advantage of at least some embodiments according to the present invention that a series of surprisingly good effects were observed when of combining factors, confirming the concept.

The present invention also relates to a conditioning system, comprising an irrigation unit for irrigating at least part of the area of surgery, the irrigation unit comprising an irrigation liquid comprising a pH buffering liquid. Such irrigation may for example be performed for cooling or moistening, although embodiments are not limited thereto.

The conditioning system also can be an insufflator as used during laparoscopic surgery and suited for delivering different gases in which the gas mixing unit is placed before the insufflator.

The conditioning system furthermore may comprise a gas supply system adapted to be used in open surgery. A gas diffuser may be placed deep in the surgical wound and a slow flow (1 L/min) of gas (CO2 and N2O being heavier than air) will progressively fill up the cavity up to the edge of a draping tissue designed for open surgery. This draping tissue should be like an aquarium. Around the wound the edges of the draping tissue should extend at least 10 and preferably 20 cm above the incision. The edges should be soft in order not to hinder the surgeon. The opening should be variable in diameter since a smaller diameter will prevent mixing of the gas with the air. The extending part should have a covered compartment in order to limit the contact between bowels and the ambient air. Around the upper part suction should be applied in order to limit at maximum leakage of N2O into the theatre environment.

One additional component may be a temperature controller and heating and/or cooling element. The conditioner may be adapted for keeping the cavity where surgery is taking place in a temperature range between 28° and 32°, advantageously in a temperature range of 30° to 31°. Under such conditions, cells are more resistant to metabolic damage at lower temperature. Cooling may be performed using a moistening means, such as for example a sprinkler, although embodiments of the present invention are not limited thereto. Advantageously, the cooling is performed separately from the gas conditioning since using the gas as a cooling means, would result in desiccation due to heating of the gas upon entrance of the cavity.

A conditioning system as described above typically can be placed between the insufflator or supply for the gas used for flowing in or over the cavity where surgery is taking place and the patient. The conditioning system in one embodiment may be adapted for first adding $N_2O$ and $O_2$ to the carrier gas, e.g. $CO_2$, which is subsequently humidified and delivered to the patient at 30-32° C. with 100% RH.

The moistening means, e.g. sprinkler, can also be used to deliver continuously medicines or other chemical or biological components. Alternatively or in addition thereto a separate drug administering means also may be part of the conditioning system. The drug administering means, separately and/or included in the moistening means, may be adapted for administering one or more of anti-oxidants, dexamethasone, calcium channel blockers and phospholipids, Heparin and anti-angeiongic factors. Particular dosing means for guaranteeing that an appropriate dose is delivered, can be included. The conditioning means furthermore may comprise a separation means for separating areas not involved in the surgery from the area involved in the surgery. Also a means for providing a barrier gel may be included.

The conditioning system may furthermore comprise an aspiration means for aspiration of gas and disposal, as for example when applicable a smoke plume generated by vaporization of tissue as occurs during electrosurgery or during $CO_2$ or other laser surgery, typically is considered potentially harmful even carcinogenic upon inhalation, or to avoid, when applicable, $N_2O$ from flowing freely in air. During laparoscopy aspiration of gas and disposal can easily be done using the endoscopic system. The gas could be reused in closed circuit after filtrating of particulates but this is not done until today since the gas would have to be recompressed for in an insufflator for endoscopic surgery. In open surgery however, one can take advantage of the density of $CO_2$ and $N_2O$ and the conditioning system thus may comprise an aspiration system, for applying aspiration e.g. a circular aspiration system on and around the operation wound. This not only would prevent the $N_2O$ flowing into the operating theatre but would in addition protect the surgeon from inhalation of particulates generated by vaporization, another advantage.

It also is advantageous that the components of the conditioning do not substantially interfere with the tools to be used by the surgery, so that no disturbing effect is induced for the surgeon.

In another aspect, the present invention also relates to a product for use during surgery for preventing mesothelial cell trauma. The product is an irrigation liquid for irrigating at least part of the area of surgery, the irrigation liquid comprising a pH buffering liquid. Such liquids may e.g. be liquids with a higher bicarbonate content. Such a product may be part of a set of products for use during surgery for preventing mesothelial cell trauma, such a kit of parts further comprising one or more of a gas mixture for use as a pneumoperitoneum comprising between 1 and 29 volume percentage of N2O and comprising between 1 and 6 volume percentage of oxygen, anti-oxidants, such as vitamin C or vitamin En, a rinsing fluid comprising Heparin whereby the rinsing fluid may also be the irrigation fluid, a separation means for separating areas not involved in the surgery from the area involved in the surgery such as for example the separation means discussed above, one or more of Dexamethasone, calcium channel blockers and phospholipids, barriers for preventing noxious substances to reach the traumatized area such as for example barrier gels, flotation agents for diluting noxious substances, and/or anti angiogenic agents, such as for example anti VEGF or anti PLFG monoclonals. In a particular example, the set of products comprises each of these products described above. Such a set of products may encourage the user for applying all conditioning techniques, which combined provide an very good or even optimum conditioning.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage.

The foregoing description details certain embodiments of the invention. It will be appreciated, however, that no matter how detailed the foregoing appears in text, the invention may be practiced in many ways, and is therefore not limited to the embodiments disclosed. It should be noted that the use of particular terminology when describing certain features or aspects of the invention should not be taken to imply that the terminology is being re-defined herein to be restricted to include any specific characteristics of the features or aspects of the invention with which that terminology is associated.

The invention claimed is:

1. A method for preventing mesothelial cell trauma, the method comprising applying a pool of conditioning techniques prior and/or during surgery, wherein the pool of conditioning techniques comprises at least applying an irrigation liquid to irrigate at least part of the area of surgery wherein the irrigation liquid is a pH buffering liquid, applying a pneumoperitoneum comprising between 1 and 29 volume percent $N_2O$, administering anti-oxidants before and/or during the surgery, rinsing using a rinsing fluid comprising Heparin, separating areas not involved in the surgery from the area involved in the surgery, administering one or more of Dexamethasone, calcium channel blockers and phospholipids, applying barriers for preventing noxious substances from reaching any traumatized area and/or wherein flotation agents are used for diluting noxious substances, administering anti angiogenic agents.

2. A method according to claim 1, wherein applying a pneumoperitoneum comprises applying a pneumoperitoneum further comprising between 1 and 6 volume percent oxygen for preventing hypoxia in deeper layers.

3. A method according to claim 1, wherein said anti-oxidants are vitamin C and/or vitamin E.

4. A method according to claim 1, wherein the heparin is a high molecular weight heparin, the high molecular weight heparin having a molecular weight of more than 150,000 daltons.

5. A method according to claim 1, wherein said anti angiogenic agents are anti VEGF or anti PLFG monoclonals.

6. A method according to claim 2, applying a pneumoperitoneum comprising between 1 and 6 volume percent oxygen for thus preventing bowel perforation and ovarfian damage and decreased ovarian reserve.

* * * * *